US010314561B2

(12) United States Patent
Itoh et al.

(10) Patent No.: US 10,314,561 B2
(45) Date of Patent: Jun. 11, 2019

(54) TOMOGRAPHIC IMAGE GENERATION DEVICE AND CONTROL METHOD

(71) Applicant: TERUMO KABUSHIKI KAISHA, Shibuya-ku (JP)

(72) Inventors: Ema Itoh, Hadano (JP); Isao Mori, Chofu (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1105 days.

(21) Appl. No.: 14/488,909

(22) Filed: Sep. 17, 2014

(65) Prior Publication Data

US 2015/0005627 A1  Jan. 1, 2015

Related U.S. Application Data

(63) Continuation of application No. PCT/JP2013/002006, filed on Mar. 25, 2013.

(30) Foreign Application Priority Data

Mar. 26, 2012 (JP) .................. 2012-069143

(51) Int. Cl.
*A61B 8/00* (2006.01)
*A61B 8/12* (2006.01)
(Continued)

(52) U.S. Cl.
CPC .......... *A61B 8/4416* (2013.01); *A61B 5/0035* (2013.01); *A61B 5/0066* (2013.01);
(Continued)

(58) Field of Classification Search
None
See application file for complete search history.

(56) References Cited

U.S. PATENT DOCUMENTS 5,163,421 A * 11/1992 Bernstein ............... A61B 8/481
606/128
5,357,550 A 10/1994 Asahina et al.
(Continued)

FOREIGN PATENT DOCUMENTS

EP  1 810 610 A1  7/2007
JP  5-64638 A  3/1993
(Continued)

OTHER PUBLICATIONS

International Search Report (PCT/ISA/210) dated Jun. 18, 2013, by the Japanese Patent Office as the International Searching Authority for International Application No. PCT/JP2013/002006.
The extended European Search Report dated Oct. 29, 2015, by the European Patent Office in corresponding European Patent Application No. 13768250.6-1660. (6 pages).

*Primary Examiner* — Jonathan Cwern
(74) *Attorney, Agent, or Firm* — Buchanan Ingersoll & Rooney PC

(57) ABSTRACT

A tomographic image generation device acquires ultrasonic wave data and interference light data to be used for generating a tomographic image for one line in respective rotation positions of the transmitting and receiving unit by performing sampling respectively on an ultrasonic wave echo signal and an interference light signal obtained by driving the ultrasonic wave transmitting and receiving unit and the optical transmitting and receiving unit while rotating the transmitting and receiving unit. Then, the tomographic image generation device controls operation timing of the acquisition means so that a sampling period for performing sampling on the interference light signal for one line and a predetermined period from driving of the ultrasonic wave transmitting and receiving unit for ultrasonic wave oscillation are not overlapped.

18 Claims, 10 Drawing Sheets

(51) Int. Cl.
*A61B 5/00* (2006.01)
*A61B 8/08* (2006.01)

(52) U.S. Cl.
CPC .......... *A61B 5/0073* (2013.01); *A61B 5/0084* (2013.01); *A61B 8/12* (2013.01); *A61B 8/445* (2013.01); *A61B 8/4461* (2013.01); *A61B 8/4483* (2013.01); *A61B 8/5207* (2013.01); *A61B 8/54* (2013.01); *A61B 8/0891* (2013.01)

(56) References Cited

U.S. PATENT DOCUMENTS

| | | | | |
|---|---|---|---|---|
| 2007/0135887 A1* | 6/2007 | Maschke | ............... | A61B 8/12 623/1.11 |
| 2007/0244391 A1* | 10/2007 | Hirota | ............... | A61B 5/0066 600/443 |
| 2012/0172698 A1* | 7/2012 | Teo | ............... | A61B 5/0066 600/407 |

FOREIGN PATENT DOCUMENTS

| | | | |
|---|---|---|---|
| JP | 11-56752 A | | 3/1999 |
| JP | 2002-153472 A | | 5/2002 |
| JP | 2005-224399 A | | 8/2005 |
| JP | 2008-142454 A | | 6/2008 |
| WO | WO 2007/023878 A1 | | 3/2007 |
| WO | 2012/091903 A1 | | 7/2012 |

* cited by examiner

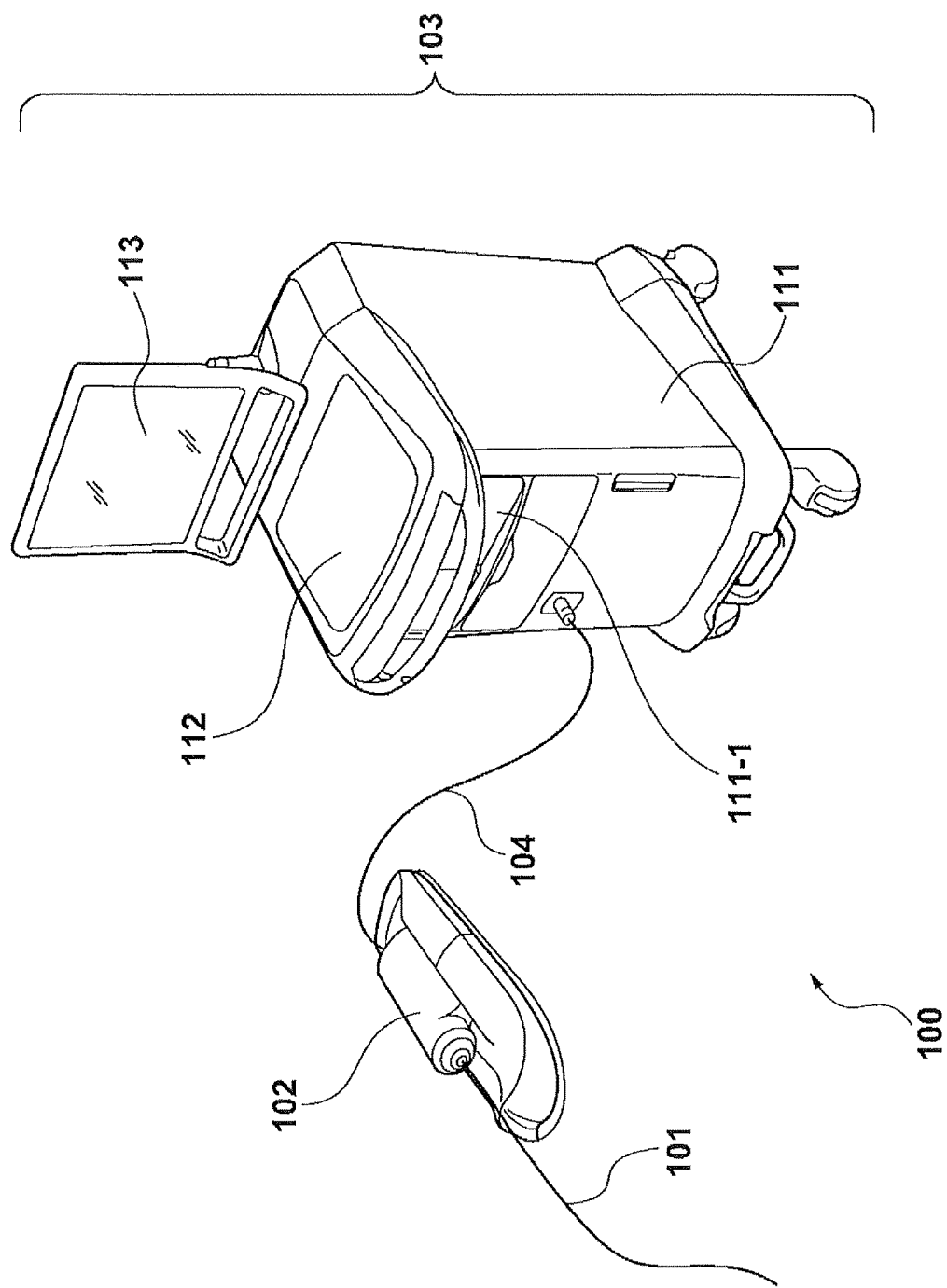
[FIG. 1]

[FIG. 2]
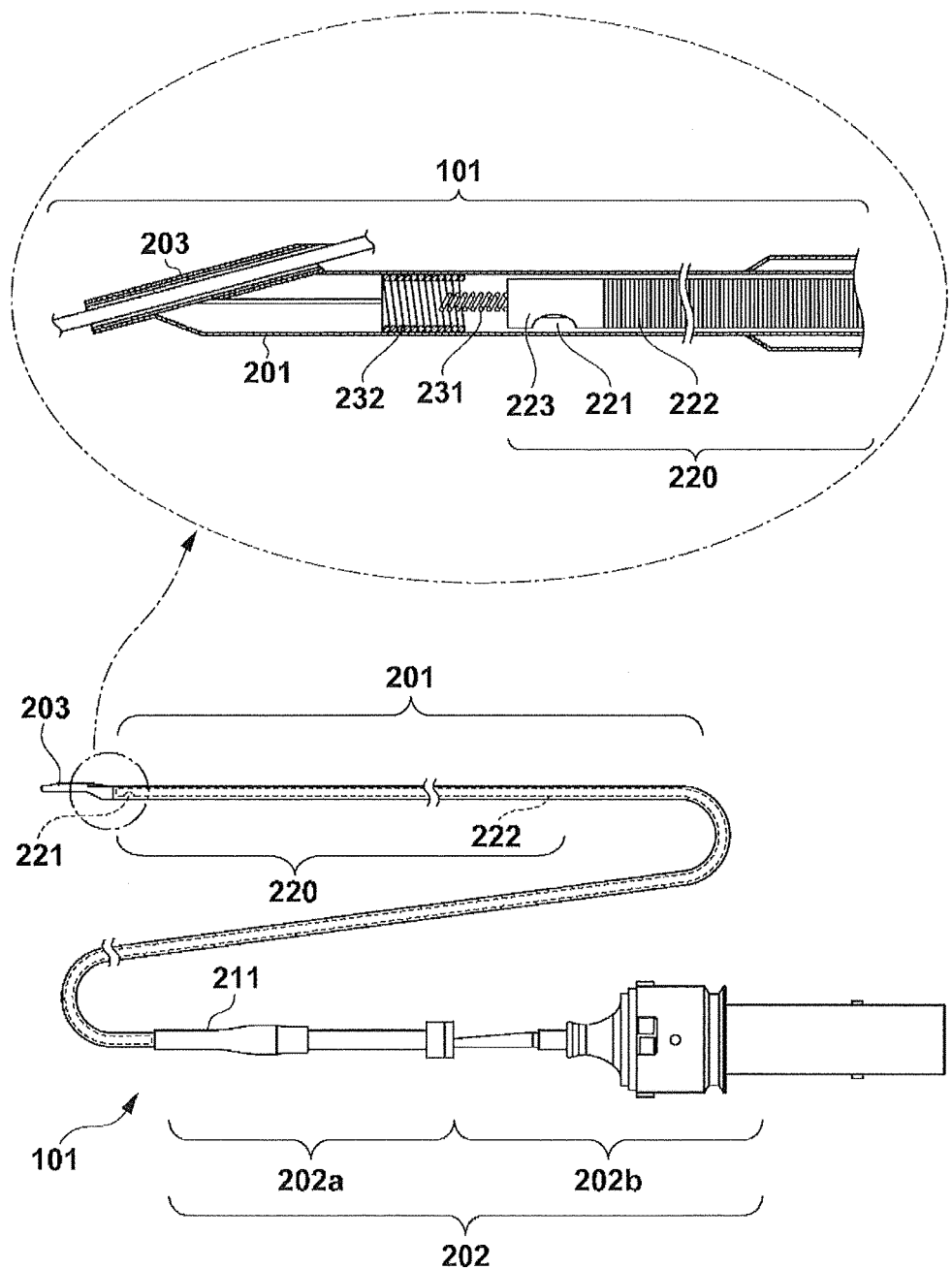

[FIG. 3]
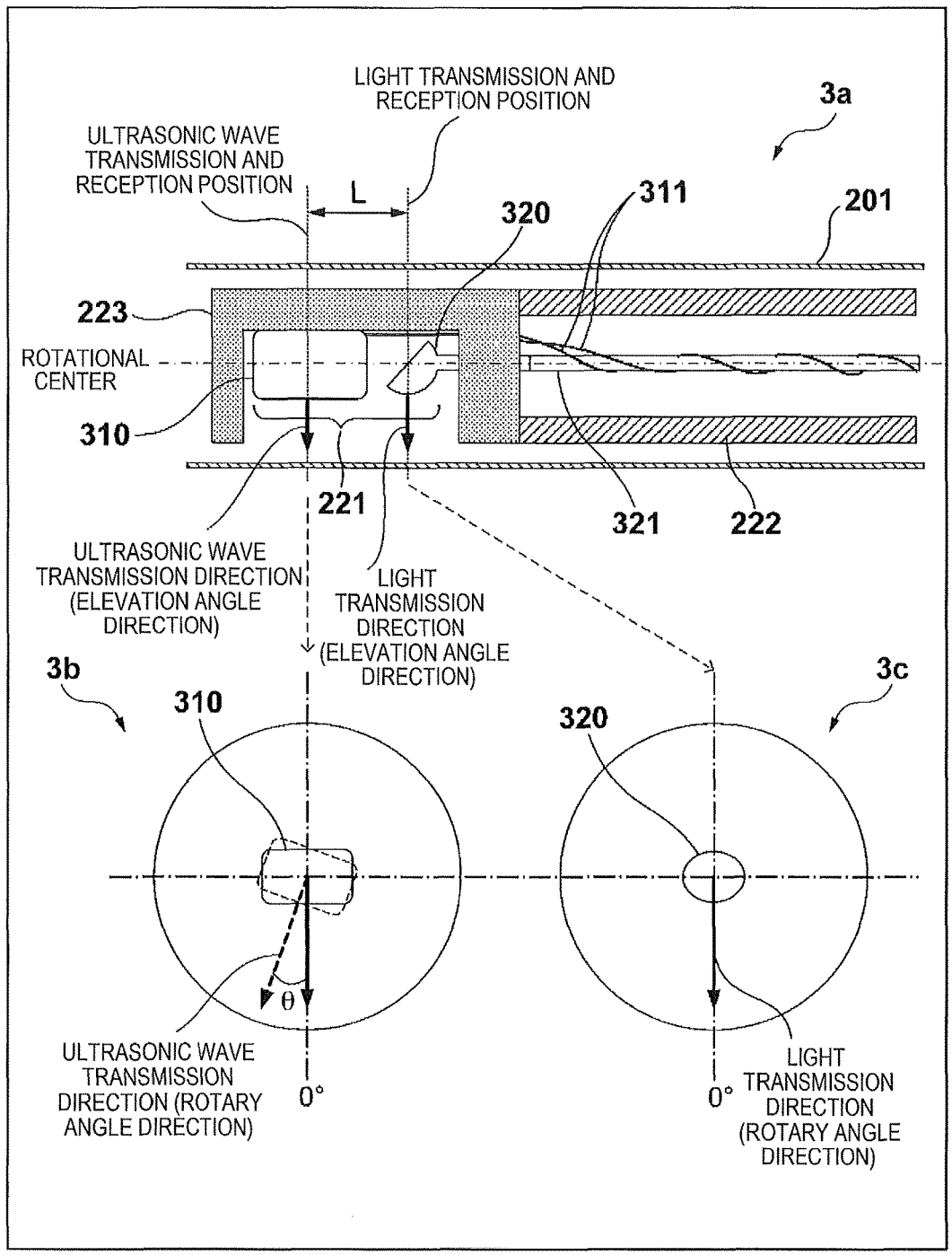

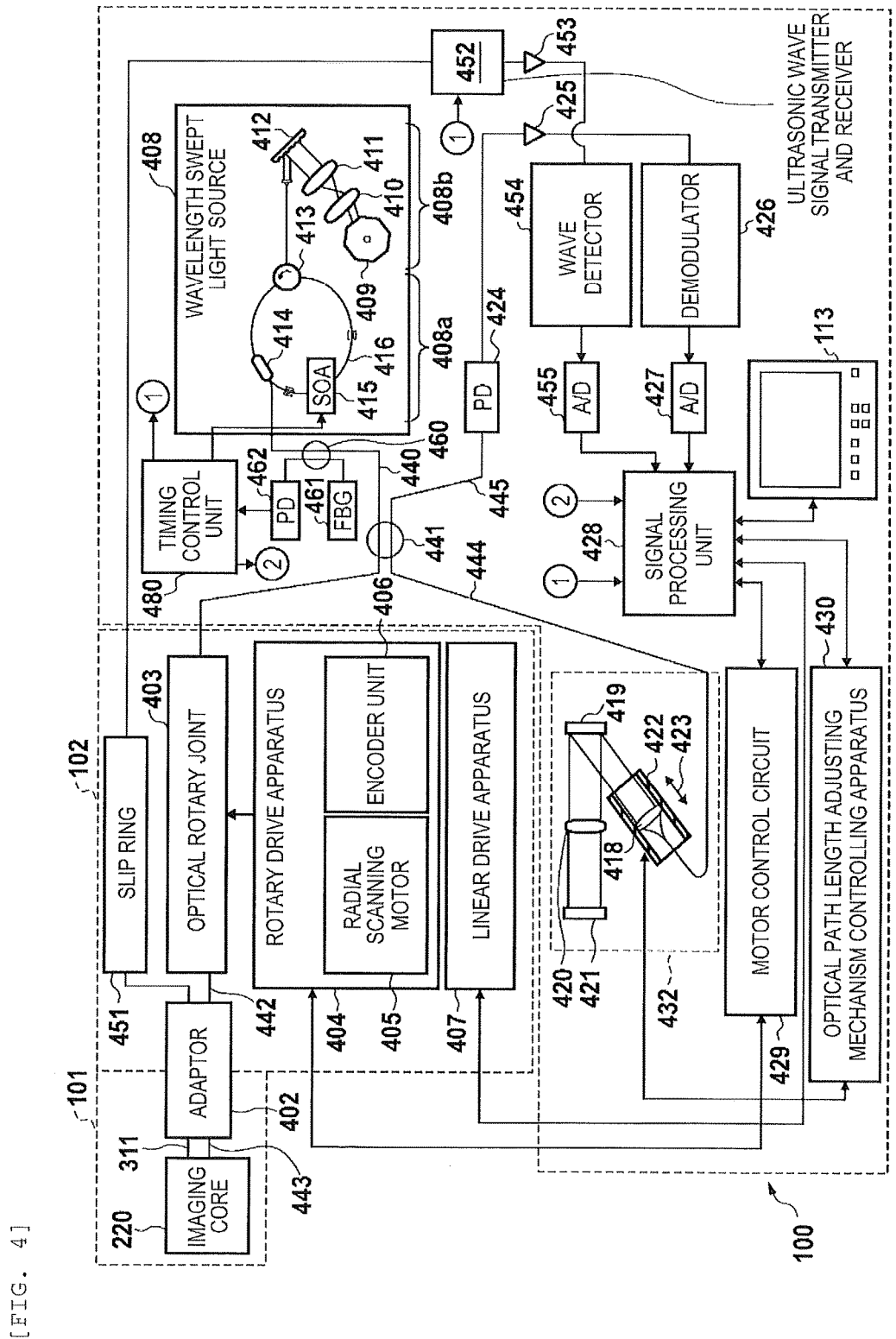
[FIG. 4]

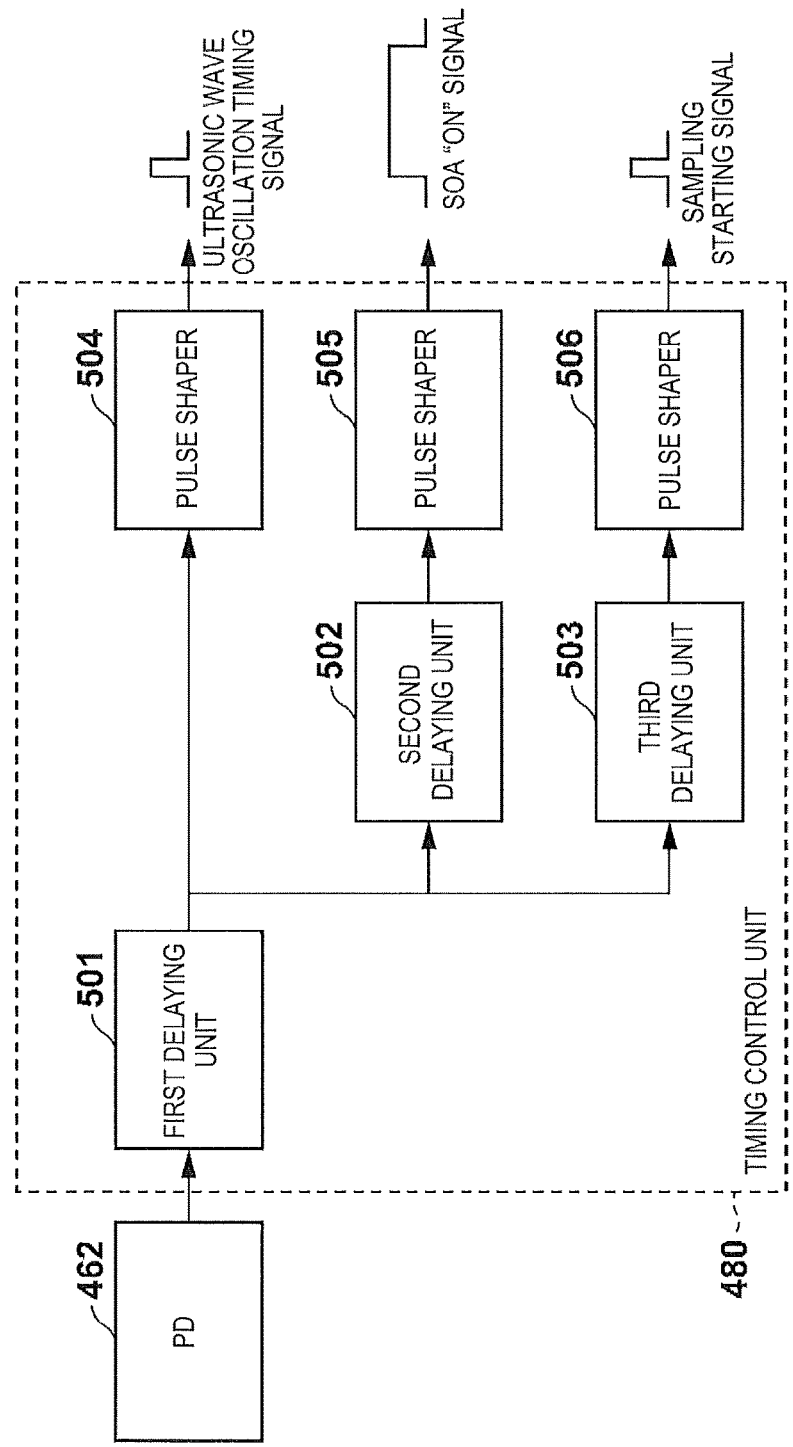
[FIG. 5]

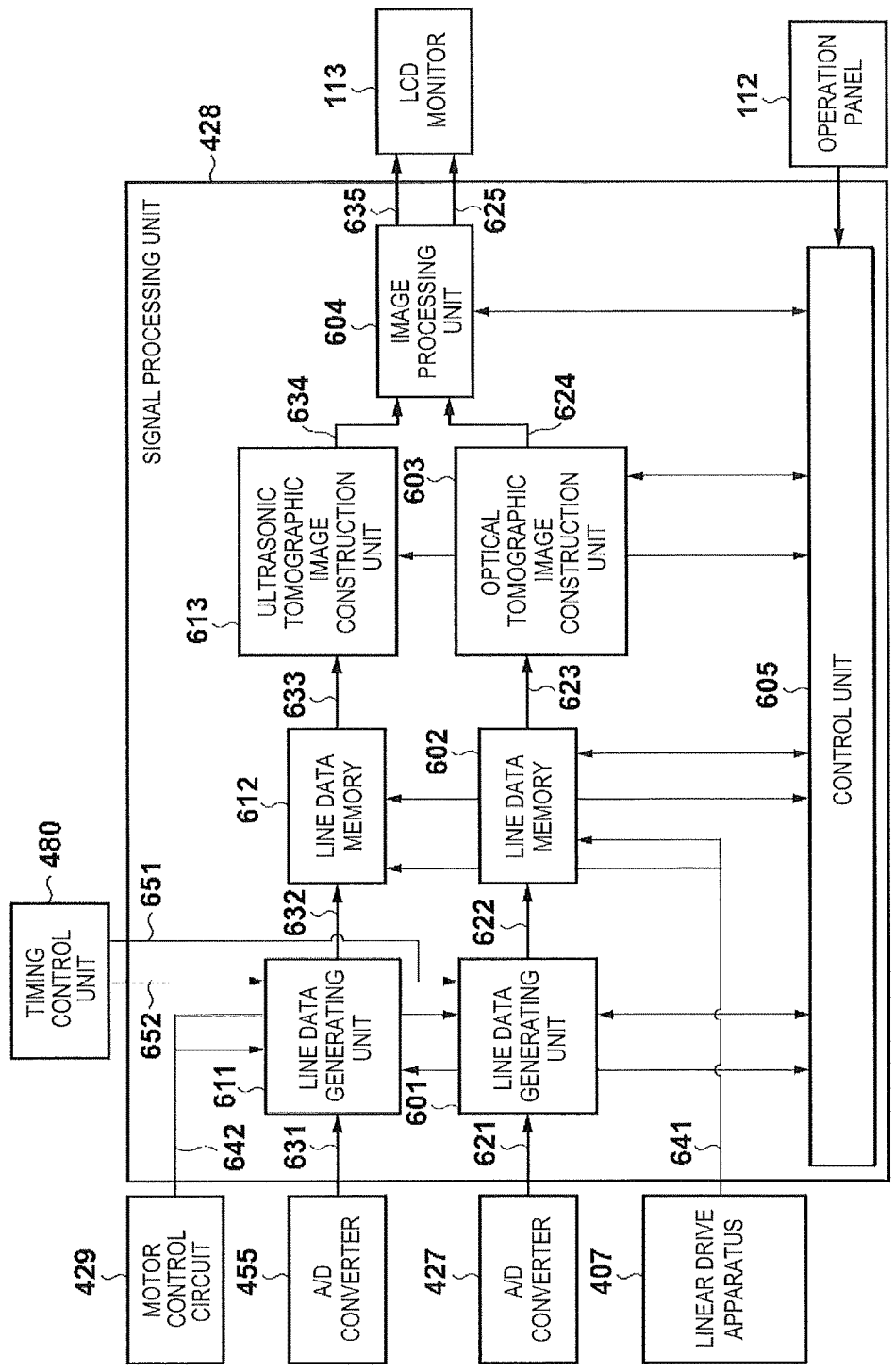
[FIG. 6]

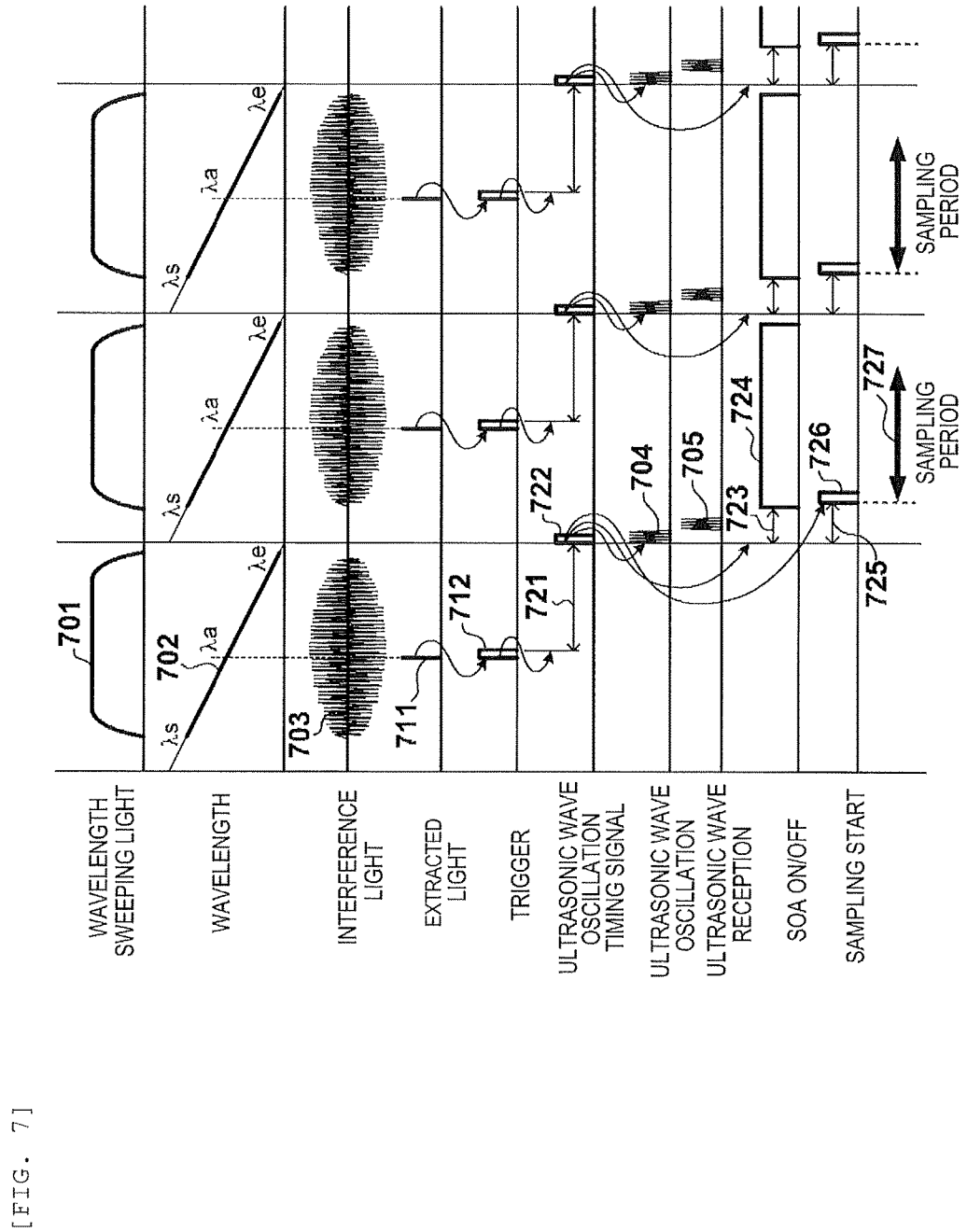
[FIG. 7]

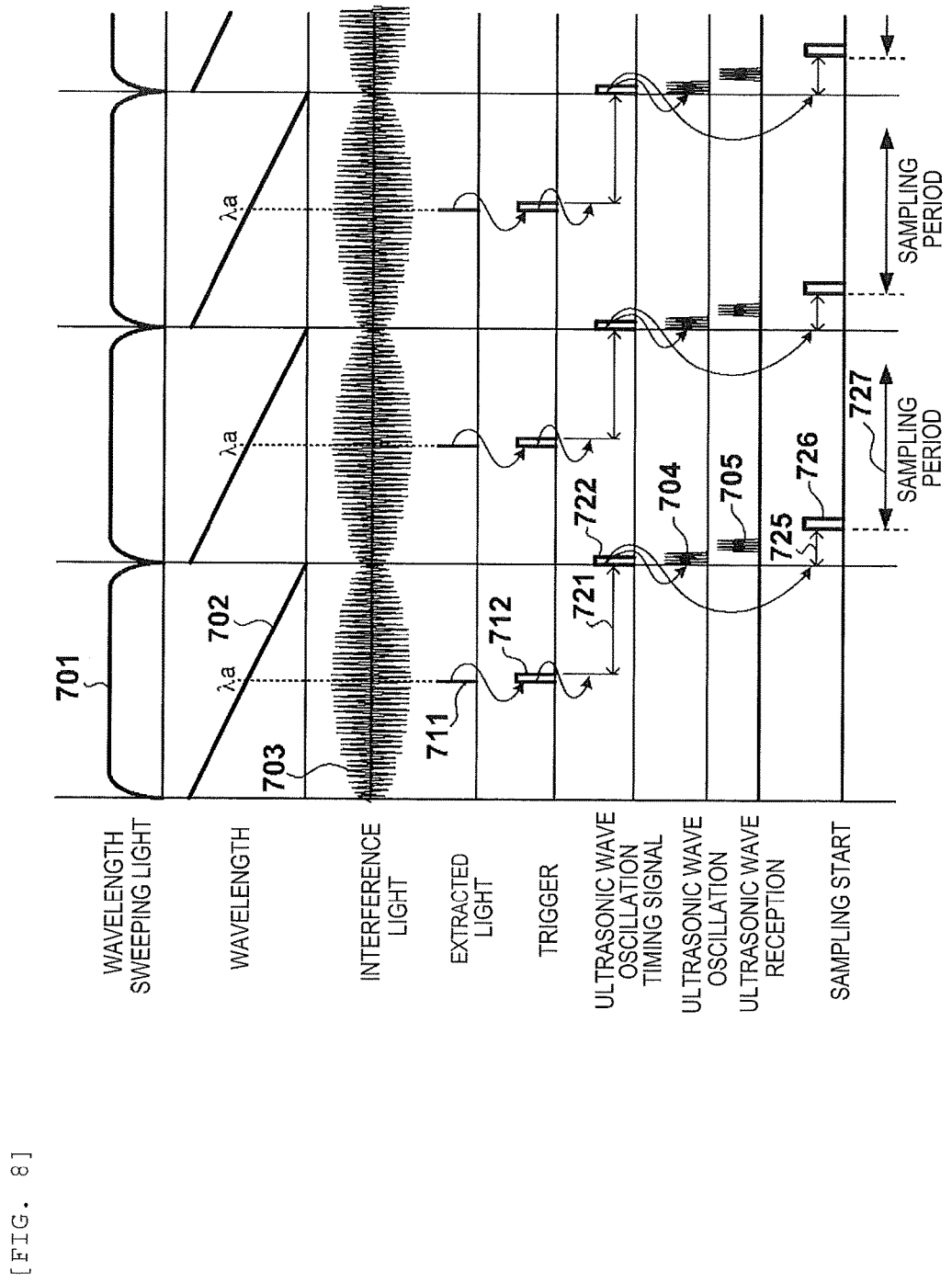
[FIG. 8]

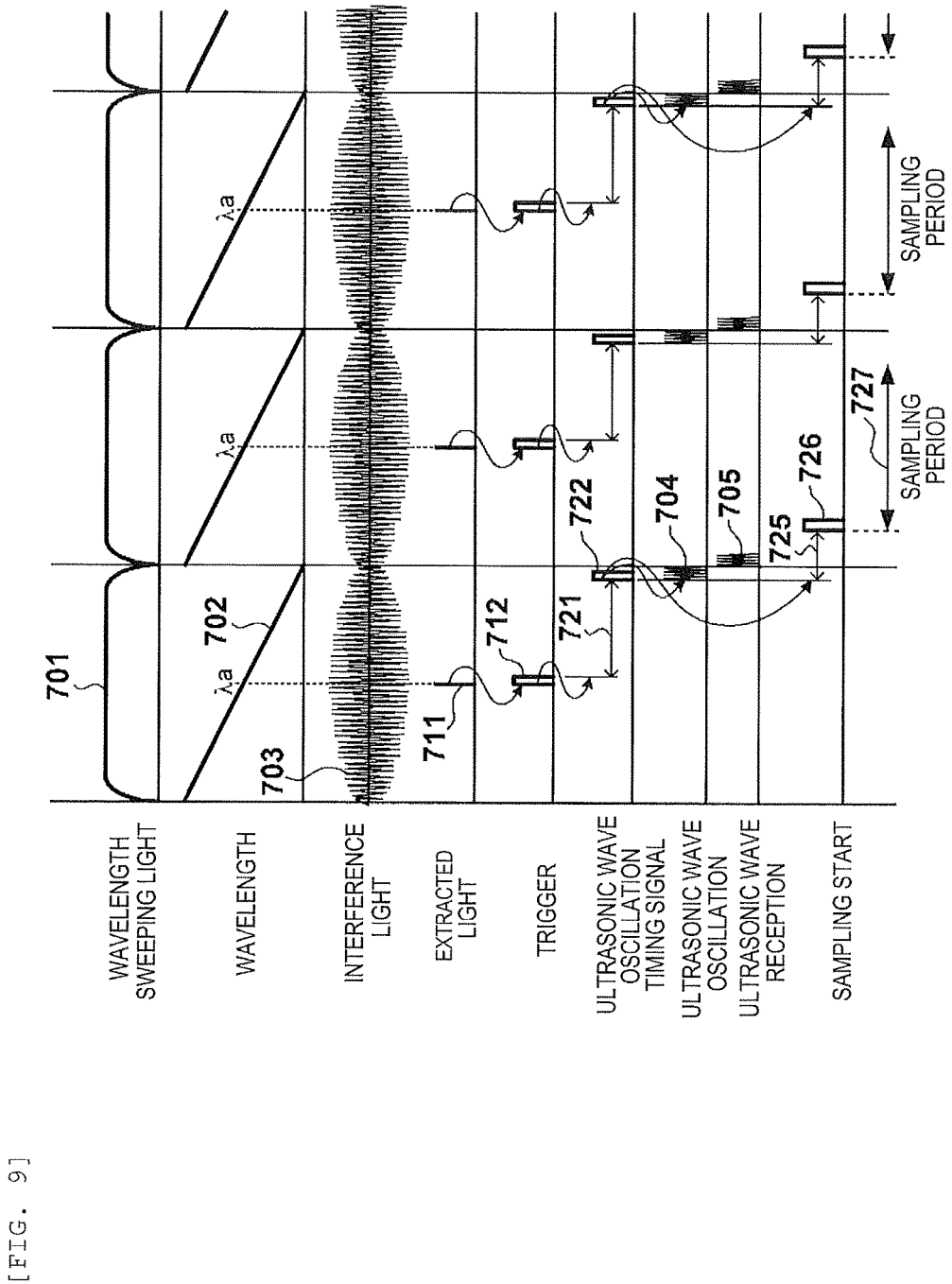
[FIG. 9]

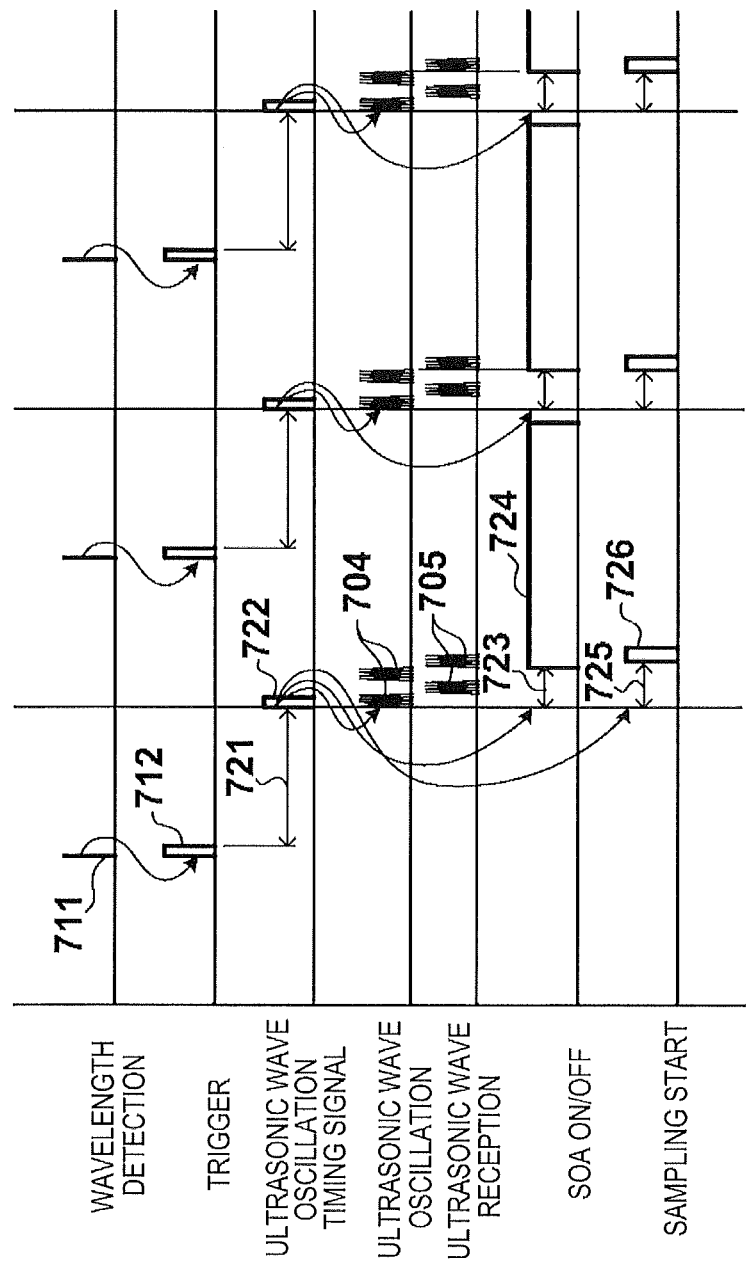

TOMOGRAPHIC IMAGE GENERATION DEVICE AND CONTROL METHOD

CROSS-REFERENCES TO RELATED APPLICATIONS

This application is a continuation of International Application No. PCT/JP2013/002006 filed on Mar. 25, 2013, and claims priority to Japanese Application No. 2012-069143 filed on Mar. 26, 2012, the entire content of both of which is incorporated herein by reference.

TECHNICAL FIELD

The present application relates to a tomographic image generation device that generates a tomographic image using an ultrasonic wave and a tomographic image using interference light, and a control method thereof.

BACKGROUND DISCUSSION

In the related art, an imaging apparatus for diagnosis that generates a tomographic image is widely used for arteriosclerosis diagnosis, for surgery diagnosis at the time of treatment in a blood vessel by a high-performance catheter such as a balloon catheter, or stent, or for confirmation of a surgery result. As an imaging apparatus for diagnosis described above, an ultrasonic diagnostic apparatus (Intra Vascular Ultra Sound: IVUS), an optical interference tomography diagnostic apparatus (Optical Coherence Tomography: OCT), or the like is used in the blood vessel, and the apparatuses have characteristics different from each other.

Recently an imaging apparatus for diagnosis combining the IVUS function and the OCT function has been suggested (For example, see Japanese Patent Application Publication No. 11-56752 and Japanese Patent Application Publication No. 2002-153472). The imaging apparatus for diagnosis described above can generate a tomographic image that encourages both of the characteristic of the IVUS that can measure a high depth region and the characteristic of the OCT that can measure an area at a high resolution. By encouraging advantages of both of the IVUS and the OCT, it is possible to effectively observe a state of, for example, a plaque or the like.

SUMMARY

As described above, in order to observe tomographic images from both the IVUS and the OCT, it is preferable that the observation directions of both the IVUS and the OCT be the same direction. However, if light is radiated to a medium to which an ultrasonic wave is radiated, the light is modulated, and a negative influence is caused in the optical interference tomographic image generated by the OCT. This is because a refractive index of a structure becomes sparse or dense, an original optical path changes, or a frequency is modulated, due to the ultrasonic wave (acousto-optic effect). Therefore, as described above, if the observation directions of both of the IVUS and the OCT are matched or approximated, the image quality of the OCT is deteriorated due to the acousto-optic effect.

While taking the problems described above into consideration, an object of the present application is to decrease or remove the influence of the acousto-optic effect, when a tomographic image using an ultrasonic wave and a tomographic image using light interference are acquired.

In order to achieve the object described above, the tomographic image generation device discussed here includes a configuration as below. That is, a tomographic image generation device includes a probe unit including a transmitting and receiving unit in which an ultrasonic wave transmitting and receiving unit that performs ultrasonic wave transmission and reception and an optical transmitting and receiving unit that performs light transmission and reception are disposed, ultrasonic wave data acquisition means for acquiring ultrasonic wave data to be used for generating a tomographic image for one line in respective rotation positions of the transmitting and receiving unit by performing sampling on an ultrasonic wave echo signal obtained from the ultrasonic wave transmitting and receiving unit caused to be driven while rotating, interference light data acquisition means for acquiring interference light data by performing sampling on an interference light signal obtained from the optical transmitting and receiving unit caused to be driven while rotating and a timing control unit configured to control operation timing of the ultrasonic wave data acquisition means and the interference light data acquisition means so that a sampling period for performing sampling on the interference light signal for one line and a predetermined period from driving of the ultrasonic wave transmitting and receiving unit for ultrasonic wave oscillation for the one line do not overlap.

It is possible to decrease or remove the influence of the acousto-optic effect when a tomographic image using an ultrasonic wave and a tomographic image using light interference are acquired.

Other characteristics or advantages are as described below with reference to the accompanied drawings. In addition, in the accompanied drawings, the same or similar configurations are denoted by the same reference numerals.

BRIEF DESCRIPTION OF DRAWINGS

Accompanied drawings are included in the specification, form a part of the same, present embodiments of the present application, and describe principles of the present application together with the descriptions of the embodiments.

FIG. 1 is a diagram illustrating a configuration of an external appearance of an imaging apparatus for diagnosis 100 according to an embodiment.

FIG. 2 is a diagram illustrating an entire configuration and a cross-sectional configuration of a distal end portion of a probe unit.

FIG. 3 is a diagram illustrating a cross-sectional configuration of an imaging core and dispositions of an ultrasonic wave transmitting and receiving unit and an optical transmitting and receiving unit.

FIG. 4 is a diagram illustrating an exemplary functional configuration of the imaging apparatus for diagnosis 100 according to the embodiment.

FIG. 5 is a block diagram illustrating an exemplary configuration of a timing control unit.

FIG. 6 is a block diagram illustrating an exemplary configuration of a signal processing unit according to the embodiment.

FIG. 7 is a timing chart illustrating timing control performed by the timing control unit.

FIG. 8 is a timing chart illustrating timing control performed by the timing control unit.

FIG. 9 is a timing chart illustrating timing control performed by the timing control unit.

FIG. 10 is a timing chart illustrating timing control performed by the timing control unit.

DETAILED DESCRIPTION

Hereinafter, exemplary embodiments are described with reference to the drawings.

1. Configuration of External Appearance of Imaging Apparatus for Diagnosis

FIG. 1 is a diagram illustrating a configuration of an external appearance of an imaging apparatus for diagnosis (imaging apparatus for diagnosis including an IVUS function and an OCT function) 100 as a tomographic image generation device according to an embodiment.

As illustrated in FIG. 1, the imaging apparatus for diagnosis 100 includes a probe unit 101, a scanner & pull-back unit 102, and an operation control apparatus 103. The scanner & pull-back unit 102 and the operation control apparatus 103 are connected to each other through a signal line 104 (including an optical fiber and an electrical signal line) so that various signals can be transmitted.

The probe unit 101 is directly inserted to the inside of a body cavity such as a blood vessel to be used. An imaging core including an ultrasonic wave transmitting and receiving unit and an optical transmitting and receiving unit is inserted into the probe unit 101. The ultrasonic wave transmitting and receiving unit transmits an ultrasonic wave to the body cavity based on a pulse signal, and receives a reflected wave from the inside of the body cavity. Additionally, the optical transmitting and receiving unit continuously transmits transmitted light (measurement light) to the inside of the body cavity and continuously receives reflected light from the inside of the body cavity. The imaging apparatus for diagnosis 100 obtains the tomographic image of the inside portion of the body cavity by using the imaging core.

The scanner & pull-back unit 102 is detachably provided with the probe unit 101, and regulates a radial movement (a movement in an axial direction and a movement in a rotation direction inside the body cavity) of the imaging core inserted into the probe unit 101 by driving a built-in motor. Additionally, the scanner & pull-back unit 102 transmits an ultrasonic wave echo signal based on the reflected wave received in the ultrasonic wave transmitting and receiving unit and the reflected light received in the optical transmitting and receiving unit, to the operation control apparatus 103 through the signal line 104.

The operation control apparatus 103 has a function of inputting various set values when performing the measurement and a function of processing data obtained by the measurement and displaying the data as tomographic images of the inside of the body cavity. In the operation control apparatus 103, reference number 111 denotes a main body control unit, and the main body control unit generates ultrasonic wave data based on a reflected wave obtained by the measurement and processes line data generated based on the ultrasonic wave data so as to generate an ultrasonic tomographic image. Further, the main body control unit generates interference light data by interfering with the reflected light obtained by the measurement and reference light obtained by being separated from light from a light source and generates an optical tomographic image by processing line data generated based on the interference light data. Here, the line data are defined as, for example, data arrays that form lines from the center to the end of the tomographic image.

Reference number 111-1 denotes a printer & DVD recorder, and the printer & DVD recorder prints process results in the main body control unit 111 or stores the process results as data. Reference number 112 denotes an operation panel, and a user inputs various set values and instructions through the operation panel 112. Reference number 113 is an LCD monitor as a display device, and the LCD monitor displays the tomographic image generated in the main body control unit 111.

2. Entire Configuration of Probe Unit and Cross-sectional Configuration of Distal End Portion of the Probe Unit Next, the entire configuration of the probe unit 101 and a cross-sectional configuration of a distal end portion of the probe unit 101 are described with reference to FIG. 2. As illustrated in FIG. 2, the probe unit 101 includes a long catheter sheath 201 to be inserted to the inside of the body cavity such as a blood vessel, and a connector unit 202 that is not inserted into the body cavity such as a blood vessel. The connector unit 202 is disposed near the user's hand side so as to be operated by the user. A tube for guide wire lumen 203 that configures a guide wire lumen is provided on the distal end of the catheter sheath 201. That is, the distal end of the catheter sheath 201 includes a tube 203 possessing a guide wire lumen configured to receive a guide wire. The catheter sheath 201 forms a lumen that continues from the connection section with the tube for guide wire lumen 203 to the connection section with the connector unit 202.

An imaging core 220 that includes a transmitting and receiving unit 221 in which the ultrasonic wave transmitting and receiving unit for transmitting and receiving an ultrasonic wave and the optical transmitting and receiving unit for transmitting and receiving light are disposed, and a coil-shaped drive shaft 222 that includes an electric signal cable and an optical fiber cable in the inside portion and that transfers rotary drive force for rotating the cables is inserted into the inside portion of the lumen of the catheter sheath 201 throughout almost the entire length of the catheter sheath 201.

The connector unit 202 includes a sheath connector 202a that is configured on a proximal end of the catheter sheath 201 in an integrated manner and a drive shaft connector 202b that is configured on a proximal end of the drive shaft 222 in a manner of rotatably fixing the drive shaft 222. An anti-kink protector 211 is provided on the boundary portion between the sheath connector 202a and the catheter sheath 201. According to this, predetermined rigidity is maintained, and bending (kinks) caused by the change of the rapid physical property can be prevented. The proximal end of the drive shaft connector 202b is detachably attached to the scanner & pull-back unit 102.

Next, the cross-sectional configuration of the distal end portion of the probe unit 101 is described. The imaging core 220 including a housing 223 that has the transmitting and receiving unit 221 in which the ultrasonic wave transmitting and receiving unit that transmits and receives the ultrasonic wave and the optical transmitting and receiving unit that transmits and receives light are disposed, and the drive shaft 222 that transfers rotary drive force for rotating the housing 223 is inserted into the inside portion of the lumen of the catheter sheath 201, throughout the entire length, so as to form the probe unit 101.

The transmitting and receiving unit 221 transmits an ultrasonic wave and light to a tissue in the body cavity, and receives a reflected wave and reflected light from the tissue in the body cavity. The drive shaft 222 is formed in a coil shape, and an electric signal cable and an optical fiber cable (an optical fiber cable in a single mode) are provided in the inside portion of the drive shaft 222.

The housing 223 has a shape having notches in a portion of a short cylindrical metal pipe, and is formed by performing carving a metal ingot or metal powder injection molding (MIM). The housing 223 has the ultrasonic wave transmitting and receiving unit and the optical transmitting and receiving unit in the inside portion as the transmitting and receiving unit 221 and is connected to the drive shaft 222 on the proximal side. Additionally, a short coil-shaped elastic member 231 is provided on the distal side.

Since the elastic member 231 is a stainless steel wire formed into a coil shape and the elastic member 231 is provided on the distal side, when the imaging core 220 is moved back and forth, the imaging core 220 is prevented from being caught in the catheter sheath 201. Reference number 232 denotes a reinforcement coil, and the reinforcement coil is provided for the purpose of preventing the distal end portion of the catheter sheath 201 from being drastically bended.

The tube for guide wire lumen 203 has a lumen for a guide wire into which the guide wire can be inserted. The tube for guide wire lumen 203 is used for receiving the guide wire inserted into the body cavity such as the blood vessel in advance, and for causing the guide wire to guide the catheter sheath 201 to a target lesion.

The drive shaft 222 is able to cause the transmitting and receiving unit 221 to rotate and move in the axis direction with respect to the catheter sheath 201, and is configured with a multiplex and multilayer contact coil which has a characteristic of being flexible and capable of effectively transferring rotation and is made with, for example, a metal wire such as stainless steel.

3. Cross-sectional Configuration of Imaging Core

Next, the cross-sectional configuration of the imaging core 220 and disposition of the ultrasonic wave transmitting and receiving unit and the optical transmitting and receiving unit are described. FIG. 3 is a diagram illustrating the cross-sectional configuration of the imaging core and dispositions of the ultrasonic wave transmitting and receiving unit and the optical transmitting and receiving unit.

As illustrated in FIG. 3a of FIG. 3, the transmitting and receiving unit 221 provided in the housing 223 includes an ultrasonic wave transmitting and receiving unit 310 and an optical transmitting and receiving unit 320, and the ultrasonic wave transmitting and receiving unit 310 and the optical transmitting and receiving unit 320 each are disposed along the axis direction on the rotary central axis of the drive shaft 222 (on the alternate long and short dash line in FIG. 3a).

Among them, the ultrasonic wave transmitting and receiving unit 310 is disposed on the distal side of the probe unit 101 and the optical transmitting and receiving unit 320 is disposed on the proximal side of the probe unit 101, the ultrasonic wave transmitting and receiving unit 310 and the optical transmitting and receiving unit 320 are disposed in the housing 223 so that a distance between an ultrasonic wave transmission and reception position of the ultrasonic wave transmitting and receiving unit 310 and a light transmission and reception position of the optical transmitting and receiving unit 320 is L.

Additionally, the ultrasonic wave transmitting and receiving unit 310 and the optical transmitting and receiving unit 320 are attached in the housing 223 so that the ultrasonic wave transmission direction (elevation angle direction) of the ultrasonic wave transmitting and receiving unit 310 and the light transmission direction (elevation angle direction) of the optical transmitting and receiving unit 320 respectively form at about 90° with respect to the axis direction of the drive shaft 222.

Electric signal cables 311 connected to the ultrasonic wave transmitting and receiving unit 310 and an optical fiber cable 321 connected to the optical transmitting and receiving unit 320 are disposed in the inside portion of the drive shaft 222, and the electric signal cables 311 are wound around the optical fiber cable 321 in a spiral shape.

FIG. 3b of FIG. 3 is a cross-sectional view when the ultrasonic wave reception position is cut along a surface approximately orthogonal to the rotary central axis. Additionally, FIG. 3c of FIG. 3 is a cross-sectional view when the light transmission and reception position is cut along a surface approximately orthogonal to the rotary central axis. As illustrated in FIGS. 3b and 3c of FIG. 3, the ultrasonic wave transmission direction of the ultrasonic wave transmitting and receiving unit 310 and the light transmission direction of the optical transmitting and receiving unit 320 are identical with respect to the rotary direction.

In addition, in FIG. 3a of FIG. 3, it is configured that the ultrasonic wave transmitting and receiving unit 310 is disposed on the distal side of the probe unit 101, and the optical transmitting and receiving unit 320 is disposed on the proximal side of the probe unit 101. However, it may be configured that the optical transmitting and receiving unit 320 is disposed on the distal side of the probe unit 101 and the ultrasonic wave transmitting and receiving unit 310 is disposed on the proximal side of the probe unit 101. Additionally, the ultrasonic wave transmission direction (elevation angle direction) of the ultrasonic wave transmitting and receiving unit 310 and the light transmission direction (elevation angle direction) of the optical transmitting and receiving unit 320 are approximately 90°. However, the tomographic image generation device according to the present application is not limited thereto. The elevation angle directions the ultrasonic wave transmitting and receiving unit 310 and of the optical transmitting and receiving unit 320 may be deviated from 90° by several degrees in order to decrease the influence of the reflection from an inner surface of the catheter sheath 201. Additionally, in FIGS. 3b and 3c of FIG. 3, the ultrasonic wave transmission direction of the ultrasonic wave transmitting and receiving unit 310 and the light transmission direction of the optical transmitting and receiving unit 320 are identical with respect to the rotary direction. However, the device disclosed here is not limited in this way. As illustrated in FIG. 3b with a broken line, the ultrasonic wave transmission direction and the light transmission direction may be disposed to form a predetermined angle θ with respect to the rotary direction. Further, in FIGS. 3a to 3c of FIG. 3, the ultrasonic wave transmitting and receiving unit 310 and the optical transmitting and receiving unit 320 are disposed on the rotary central axis. However, the tomographic image generation device according to the present application is not limited in this way. For example, the ultrasonic wave transmitting and receiving unit 310 and the optical transmitting and receiving unit 320 may be disposed at positions separate from the rotary central axis by a certain distance. Additionally, at this point, the ultrasonic wave transmission direction (rotary angle direction) and the light transmission direction (rotary angle direction) may be arranged so that the angle difference between the ultrasonic wave transmission direction and the light transmission direction with respect to the rotary direction is θ.

4. Functional Configuration of Imaging Apparatus for Diagnosis

Next, a functional configuration of the imaging apparatus for diagnosis 100 as a tomographic image generation device according to the present embodiment is described. FIG. 4 is a diagram illustrating the functional configuration of the imaging apparatus for diagnosis 100 combining the IVUS function and the OCT (here, wavelength sweeping-type OCT as an example) function. In addition, since the imaging apparatus for diagnosis combining the IVUS function and another scheme of the OCT function also has the same functional configuration, the description thereof is omitted here.

(1) IVUS Function

The ultrasonic wave transmitting and receiving unit 310 of the imaging core 220 transmits an ultrasonic wave to a biological tissue based on a pulse wave transmitted from an ultrasonic wave signal transmitter and receiver 452, receives a reflected wave (echo) of the ultrasonic wave, and transmits the reflected wave to the ultrasonic wave signal transmitter and receiver 452 as an ultrasonic wave echo. The transmission of the pulse wave and the ultrasonic wave echo between the ultrasonic wave signal transmitter and receiver 452 and the ultrasonic wave transmitting and receiving unit 310 is performed through an adaptor 402, a slip ring 451, and the electric signal cables 311.

In addition, a rotary drive unit side of the slip ring 451 is rotatably driven by a radial scanning motor 405 of a rotary drive apparatus 404. Additionally, a rotation angle of the radial scanning motor 405 is detected by an encoder unit 406. Further, the scanner & pull-back unit 102 includes a linear drive apparatus 407, and regulates a movement of the imaging core 220 in an axial direction based on a signal from a signal processing unit 428.

Additionally, the ultrasonic wave signal transmitter and receiver 452 transmits a pulse wave based on an ultrasonic wave oscillation timing signal from a timing control unit 480 for performing oscillation driving on the ultrasonic wave transmitting and receiving unit 310 in the imaging core 220. The ultrasonic wave transmitting and receiving unit 310 oscillates the ultrasonic wave according to the pulse wave and transmits the ultrasonic wave echo signal based on the reflected wave to the ultrasonic wave signal transmitter and receiver 452. The ultrasonic wave signal transmitter and receiver 452 outputs the ultrasonic wave echo signal received from the ultrasonic wave transmitting and receiving unit 310 to an amplifier 453, and the ultrasonic wave echo signal amplified by the amplifier 453 is input into a wave detector 454 to be detected.

The device disclosed here also includes a A/D converter 455. This A/D converter 455 represents an example of an ultrasonic wave data acquisition means for acquiring ultrasonic wave data to generate a tomographic image for one line in respective rotation positions of the transmitting and receiving unit. Further, in the A/D converter 455, sampling is performed on an ultrasonic wave echo signal output from the wave detector 454 at 30.6 MHz to generate digital data. In addition, here, the sampling frequency is set to be 30.6 MHz, but the frequency is calculated on an assumption that when the speed of sound is 1530 m/sec, sampling 200 points is performed with respect to the depth of 5 mm. Accordingly, the sampling frequency is not particularly limited thereto.

The digital data based on the ultrasonic wave echo signal generated from the A/D converter 455 are input into the signal processing unit 428. In the signal processing unit 428, the digital data input from the A/D converter 455 are extracted by sampling 200 points synchronized with the ultrasonic wave oscillation timing signal generated by the timing control unit 480, and 1 line of the digital data (ultrasonic wave data) of the tomographic image is generated, and stored. Then, the signal processing unit 428 generates line data by converting the ultrasonic wave data into grayscale, collects the data for one tomographic image, forms an ultrasonic tomographic image at each position in the body cavity such as the blood vessel, and outputs the ultrasonic tomographic image at a predetermined frame rate to the LCD monitor 113.

Further, the signal processing unit 428 is connected to a motor control circuit 429, and receives a video synchronization signal of the motor control circuit 429. In the signal processing unit 428, the ultrasonic tomographic image is constructed in synchronization with the received video synchronization signal. The operations of the timing control unit 480 and the signal processing unit 428 are described below. The video synchronization signal of the motor control circuit 429 is also transmitted to the rotary drive apparatus 404, and the rotary drive apparatus 404 outputs a drive signal synchronized with the video synchronization signal.

(2) Wavelength Sweeping-type OCT Function

Reference number 408 denotes a wavelength swept light source (Swept Laser). The wavelength swept light source is a kind of Extended-cavity Laser including a light source unit (408a) having the SOA 415 (Semiconductor Optical Amplifier) and an optical fiber 416 coupled in a ring shape, and a polygon scanning filter (408b).

The light output from the SOA 415 progresses through the optical fiber 416, and enters the polygon scanning filter 408b through the optical circulator 413. The light subjected to wavelength selection in the polygon scanning filter 408b is caused to return to the light source unit 408a through the optical circulator 413, amplified in the SOA 415, and finally output from a coupler 414.

In the polygon scanning filter 408b, the wavelength is selected by the combination of a diffraction grating 412 light-splitting light and a polygon mirror 409. Specifically, the light light-split by the diffraction grating 412 is converged on a surface of the polygon mirror 409 by two lenses (410 and 411). According to this, only the light in a wavelength that is orthogonal to the polygon mirror 409 returns to the same optical path, and is output from the polygon scanning filter 408b. That is, time sweeping of the wavelength can be performed by rotating the polygon mirror 409.

The polygon mirror 409 uses, for example, a 32-sided mirror, and the number of rotations is about 50000 rpm. The high-speed and high-output wavelength sweeping can be performed by the wavelength sweeping scheme combining the polygon mirror 409 and the diffraction grating 412.

The light of the wavelength swept light source 408 output from the coupler 414 is incident on an end of the first single mode fiber 440, and output to the distal side. A first single mode fiber 440 is optically coupled to a second single mode fiber 445 and a third single mode fiber 444 in a photo coupler unit 441 positioned in the middle. The light incident on the first single mode fiber 440 is divided and transmitted into the optical path of the first single mode fiber 440 connected to an optical rotary joint 403 and the optical path of the third single mode fiber 444 by the photo coupler unit 441.

On the distal side of the first single mode fiber 440 which is farther than the photo coupler unit 441, the optical rotary joint (optical coupling unit) 403 that couples between a non-rotation section (fixed section) and a rotation section (rotary drive section) and transmits light is provided in the rotary drive apparatus 404.

Further, a fifth single mode fiber 443 (the optical fiber cable 321) of the probe unit 101 is freely detachably connected to the distal side of a fourth single mode fiber 442 in the optical rotary joint (optical coupling unit) 403 through the adaptor 402. According to this, the light from the wavelength swept light source 408 is transmitted to the fifth single mode fiber 443 that is inserted to the imaging core 220 and rotatably driven.

The light transmitted to the fifth single mode fiber 443 is radiated from the optical transmitting and receiving unit 320 of the imaging core 220 while performing radial scanning on the biological tissue in the biological lumen. Then, a portion of the reflected light dispersed on a surface or in the inside portion of the biological tissue is captured by the optical transmitting and receiving unit 320 of the imaging core 220, and returns to the first single mode fiber 440 side through a reverse optical path. Further, a portion of the reflected light returned to the first single mode fiber 440 is transferred to the second single mode fiber 445 side by the photo coupler unit 441.

In addition, the rotary drive unit side of the optical rotary joint 403 is rotatably driven by the radial scanning motor 405 of the rotary drive apparatus 404 in the same manner as the IVUS configuration.

Meanwhile, an optical path adjustment mechanism 432 that fine-adjusts an optical path length of the reference light is provided on the distal end on the opposite side of the photo coupler unit 441 of the third single mode fiber 444. When the probe units 101 are exchanged and used, so that length variations of the respective probe units 101 can be absorbed, the optical path adjustment mechanism 432 has an optical path length changing section that changes the length of the optical path corresponding to the length variations.

The third single mode fiber 444 and a collimating lens 418 are provided in an one-axis stage 422 that is freely moved in the optical axial direction as indicated by an arrow 423, and forms the optical path length changing section. Specifically, when the probe units 101 are exchanged, the one-axis stage 422 functions as an optical path length changing mechanism having a variable range of the length of the optical path as wide as the length variations of the optical paths of the probe unit 101 can be absorbed. Further, the one-axis stage 422 also includes an adjustment function for adjusting an offset. For example, even if the distal end of the probe unit 101 is not in close contact with a surface of the biological tissue, it is possible to set the probe unit 101 to be in a state of interfering with the reflected light from the surface position of the biological tissue by finely changing the length of the optical path by the one-axis stage.

The length of the optical path is fine-adjusted by the one-axis stage 422, and the light (reference light) reflected by a mirror 421 through a grating 419 and a lens 420 is mixed with the light (reflected light) that is incident from the first single mode fiber 440 side by the photo coupler unit 441 provided in the middle of the third single mode fiber 444, and the light is received by a photodiode 424 as interference light.

In this manner, the interference light received by the photodiode 424 is subjected to the photoelectric conversion, amplified by an amplifier 425, and input into a demodulator 426. The demodulator 426 performs a demodulation process of extracting only a signal portion of the interfered light, and the output is input into an A/D converter 427 as an interference light signal.

The device disclosed here also includes a A/D converter 427. This A/D converter 427 represents an example of an interference light data acquisition means for acquiring interference light data by performing sampling on an interference light signal obtained from the optical transmitting and receiving unit. The A/D converter 427 generates digital data of the interference light signal by sampling the interference light signal at, for example, 180 MHz. In addition, the sampling frequency is set to be 180 MHz on an assumption that when the repetition frequency of the wavelength sweeping is set to be 80 kHz, and about 90% of the wavelength sweeping cycle (12.5 μsec) is extracted as 2048 points of digital data. The sampling frequency is not limited particularly thereto.

The digital data based on the interference signal generated by the A/D converter 427 are input into the signal processing unit 428. The signal processing unit 428 performs sampling of 2048 points from the input digital data according to the sampling start timing generated by the timing control unit 480, and generates and stores 1 line of digital data (interference light data). Then, the signal processing unit 428 generates data (line data) in the depth direction by performing frequency decomposition on the interference light data by Fast Fourier Transform (FFT), constructs an optical tomographic image at respective positions in the body cavity such as the blood vessels by performing coordinate transformation on the data, and outputs the optical tomographic image to the LCD monitor 113 at a predetermined frame rate.

In addition, the signal processing unit 428 is further connected to an optical path length adjusting mechanism controlling apparatus 430. The signal processing unit 428 controls the position of the one-axis stage 422 through the optical path length adjusting mechanism controlling apparatus 430.

(3) with Respect to Configuration of Generating Signal for Controlling Timing

As described above, the light from the wavelength swept light source 408 output from the coupler 414 is incident on one end of the first single mode fiber 440. The first single mode fiber 440 is diverged into two at a photo coupler unit 460, and one end is guided to a Fiber Bragg Grating (FBG) 461. The FBG 461 according to the present embodiment is set to reflect only light having a specific wavelength among wavelengths (sweeping wavelength) of the output light from the wavelength swept light source 408. The reflected light is supplied to a photo detector (for example, photodiode) 462 through the photo coupler unit 460, and a trigger signal is generated as an electrical signal, and supplied to the timing control unit 480. As described above, the FBG 461 and the photo detector 462 generate the trigger signal by detecting light having a predetermined wavelength set in advance in during a single wavelength sweeping by the wavelength swept light source 408. The FBG 461 and the photo detector 462 together correspond to the detecting means.

According to the trigger signal received from the photo detector 462, the timing control unit 480 generates and outputs an ultrasonic wave oscillation timing signal, a sampling starting signal for acquiring the interference light data and an SOA "ON" signal for regulating SOA lighting time. The SOA 415 is switched on when the SOA "ON" signal is ON, and switched off when the SOA "ON" signal is OFF. Additionally, the ultrasonic wave signal transmitter and receiver 452 transmits a signal for outputting an ultrasonic wave according to the ultrasonic wave oscillation timing signal to the ultrasonic wave transmitting and receiving unit 310. Additionally, the signal processing unit 428 performs sampling on the ultrasonic wave data at the timing based on the ultrasonic wave oscillation timing signal and performs sampling on the interference light data at the timing based on the sampling starting signal.

5. Configuration of Timing Control Unit 480

FIG. 5 is a block diagram illustrating an exemplary configuration of the timing control unit 480. The trigger signal output from the photo detector 462 is input into a first delaying unit 501, delayed for a first predetermined time, and output from the first delaying unit 501. The trigger signal output from the first delaying unit 501 is shaped into a pulse having a predetermined width by a pulse shaper 504, and output as the ultrasonic wave oscillation timing signal.

The trigger signal delayed by the first delaying unit is input into a second delaying unit 502, and further delayed for a second delay time. The trigger signal delayed for the first and second delay times is shaped into a pulse having a time width corresponding to a period for setting the SOA 415 to be in the ON state in a pulse shaper 505, and is output as the SOA "ON" signal. In addition, as described below, when the SOA 415 is continuously switched on, the configuration may be omitted.

Further, the trigger signal delayed by the first delaying unit is also input into a third delaying unit 503, and delayed for a third delay time. The trigger signal delayed for the first and third delay times is input into a pulse shaper 506, and output as the sampling starting signal for extracting the interference light data. According to the third delay time, the interference light data can be obtained by avoiding the influence of the acousto-optic effect generated by the ultrasonic wave transmitted by the ultrasonic wave transmitting and receiving unit 310.

The relationship between respective signals generated by the timing control unit 480 and the operations of respective sections of the wavelength swept light source 408, the ultrasonic wave signal transmitter and receiver 452, and the signal processing unit 428 is described with reference to a timing chart.

6. Functional Configuration of Signal Processing Unit

Next, the functional configuration for constructing a tomographic image in the signal processing unit 428 of the imaging apparatus for diagnosis 100 is described with reference to FIG. 6. In addition, the constructing process described below may be realized by using dedicated hardware, or may be realized by using software (by executing a program by a computer).

FIG. 6 is a diagram illustrating functional configurations and associated function blocks for realizing a construction process in the signal processing unit 428 of the imaging apparatus for diagnosis 100.

As illustrated in FIG. 6, digital data 621 of the interference light signal generated in the A/D converter 427 are supplied to a line data generating unit 601 in the signal processing unit 428. The line data generating unit 601 starts sampling according to a sampling starting signal 651 from the timing control unit 480, performs sampling of 2048 points from the input digital data 621, and stores the data as one line of the interference light data in the line memory. The line data generating unit 601 is provided with, for example, a line memory for three lines, the line memories are sequentially used, and one line of the interference light data generated according to the sampling starting signal 651 is stored.

Then, the line data generating unit 601 generates the line data by using a signal of the encoder unit 406 of the radial scanning motor 405 output from the motor control circuit 429 so that the number of lines for one rotation of the radial scanning is 512. More specifically, if the timing for obtaining the line data based on the signal of the encoder unit 406 is detected, the line data generating unit 601 reads the interference light data from the line memory in which the storage of the interference light data is lastly completed at that time, among the three line memories, and generates the data (line data) in the depth direction by performing frequency decomposition on the interference light data by Fast Fourier Transformation (FFT). The generated line data are stored in a line data memory 602. In this manner, the line data based on the interference light signals in the respective rotation positions of the transmitting and receiving unit 221 are stored in the line data memory 602.

In addition, here, for example, the optical tomographic image is constructed of 512 lines. However, the optical tomographic image may be constructed of fewer or greater than 512 lines.

Line data 622 output from the line data generating unit 601 are stored in the line data memory 602 for one rotation (for 512 lines) of the radial scanning based on an instruction from a control unit 605. At this point, a pulse signal 641 output from a movement amount detector of the linear drive apparatus 407 is counted, and when the line data 622 are stored in the line data memory 602, the control unit 605 stores the line data in association with the count rates at the time of generating the respective line data 622.

After various processes (line addition-averaging process, filtering process, or the like) are performed in an optical tomographic image construction unit 603 based on the instruction from the control unit 605, line data 623 stored in association with the count rates are subjected to Rθ conversion so that the line data are sequentially output as an optical tomographic image 624.

Further, after the image process for displaying an image on the LCD monitor 113 is performed, an image processing unit 604 outputs the image to the LCD monitor 113 as an optical tomographic image 625.

In the same manner, digital data 631 generated by the A/D converter 455 is input into a line data generating unit 611 in the signal processing unit 428. According to an ultrasonic wave oscillation timing signal 652 from the timing control unit 480, the line data generating unit 611 performs sampling on the input digital data 631 of 200 points and stores the input digital data 631 in the line memory as 1 line of the ultrasonic wave data. The line data generating unit 611 is provided with, for example, line memories for 3 lines, the line memories are sequentially used, and 1 line of the ultrasonic wave data generated according to the ultrasonic wave oscillation timing signal 652 is stored.

Further, the line data generating unit 611 generates line data by using signals from the encoder unit 406 of the radial scanning motor 405 output from the motor control circuit 429 so that the number of lines for one rotation of radial scanning becomes 512. The line data generating unit 611 generates line data by using signals from the encoder unit 406 of the radial scanning motor 405 output from the motor control circuit 429 and processes ultrasonic wave data so that the number of lines for one rotation of radial scanning becomes 512. More specifically, if timing for acquiring line data is detected based on the signal of the encoder unit 406, the ultrasonic wave data is read from the line memory in which the storage of the ultrasonic wave data is lastly completed at that time, among the three line memories, and data (line data) in the depth direction is generated by performing grayscale conversion or the like on the ultrasonic wave data. The generated line data is stored in a line data memory 612. In this manner, the line data based on the ultrasonic wave echo signal with respect to the respective rotary positions of the transmitting and receiving unit 221 are stored in the line data memory 602.

Line data 632 output from the line data generating unit 611 are stored in the line data memory 612 for one rotation of the radial scanning based on the instruction from the control unit 605. At this point, the pulse signal 641 output from a movement amount detector of the linear drive apparatus 407 is counted, and when the line data 632 are stored in the line data memory 612, the control unit 605 stores the line data in association with the count rates at the time of generating the respective line data 632.

In this manner, after various processes (line addition-averaging process, filtering process, or the like) are performed in an ultrasonic tomographic image construction unit 613 based on the instruction from the control unit 605, line data 633 stored in association with the count rates are subjected to Rθ conversion so that the line data are output as an ultrasonic tomographic image 634.

Further, after the image process for displaying an image on the LCD monitor 113 is performed, an image processing unit 604 outputs the image to the LCD monitor 113 as an ultrasonic tomographic image 635.

7. Description of Timing Control by Timing Control Unit 480

FIG. 7 is a diagram illustrating operation timings of respective sections according to timing signals generated from the timing control unit 480.

Wavelength swept light 701 is output from the wavelength swept light source 408 when the SOA 415 is switched on, and the wavelength changes from a wavelength λs to a wavelength λe as indicated by a wavelength change 702. When the wavelength swept light 701 is output, interference light 703 is obtained. According to the present embodiment, the line data of the interference light 703 in a period for 1 line and the line data by an ultrasonic wave receiving signal 705 are generated, and ultrasonic transmission and reception periods and interference light data sampling periods are not overlapped so that the influence of the acousto-optic effect on the image is avoided. Further, in an example of FIG. 7, the SOA "ON" signal is set so as to prohibit the optical output of the wavelength swept light source 408 during the ultrasonic wave transmission and reception is performed (in the present example, the SOA 415 is switched off). Therefore, the influence of the light on the sound is also avoided.

As illustrated in FIG. 7, when the FBG 461 extracts light having a certain wavelength λa from the output light of the wavelength swept light source 408 and outputs the light as extracted light 711, the photo detector 462 detects the extracted light and outputs a trigger signal 712. The trigger signal 712 is supplied to the timing control unit 480, delayed for a first delay time 721 by the first delaying unit 501, and output as an ultrasonic wave oscillation timing signal 722. The ultrasonic wave signal transmitter and receiver 452 performs ultrasonic wave oscillation 704 and ultrasonic wave reception 705 by outputting the pulse wave for driving the ultrasonic wave transmitting and receiving unit 310 according to the ultrasonic wave oscillation timing signal 722. The first delay time 721 is used for generating the ultrasonic wave oscillation timing signal 722 for the next 1 line from the trigger signal 712, and set so that the ultrasonic wave oscillation timing signal 722 is generated during the unnecessary optical interference signal being generated. In this manner, the ultrasonic wave transmitting and receiving unit 310 starts the ultrasonic wave transmission and reception after the first delay time 721 passes from the generation of the trigger signal 712.

On the other hand, the trigger signal 712 delayed for the first delay time 721 is input into the second delaying unit 502, is further delayed for a second delay time 723, and is supplied to the pulse shaper 505 so that an SOA "ON" signal 724 is generated. The SOA 415 is switched on only when the SOA "ON" signal 724 is ON so that the wavelength swept light 701 is output from the wavelength swept light source 408. The second delay time 723 is set to be longer than the time assumed to be required for the ultrasonic wave transmission and reception, so that the wavelength swept light is not radiated during the ultrasonic wave transmission and reception.

Additionally, the trigger signal 712 delayed for the first delay time is input into the third delaying unit 503, and is delayed for a third delay time 725 here, so as to be a sampling starting signal 726 with respect to the signal processing unit 428. The line data generating unit 601 performs sampling 727 for storing interference light data to the line memory according to the sampling starting signal 726. The third delay time 725 is also set to include the time assumed to be required for the ultrasonic wave transmission and reception, so that optical interference signal sampling is not performed during the ultrasonic wave transmission and reception. Additionally, it is possible to avoid sampling in a transient state when the SOA is switched on, by setting the third delay time 725 to be longer than the second delay time 723. However, if such avoidance is not required, the second and third delay times may be identical (output signals from the same delay unit may be used). As described above, timing is controlled by the third delay time 725, so that a sampling period 727 for performing sampling on the interference light signal for one line and a certain predetermined period from the driving of the ultrasonic wave transmitting and receiving unit 310 for the ultrasonic wave oscillation are not overlapped (=third delay time).

In addition, in FIG. 7, though the light emission from the light source is stopped by switching off the SOA 415 at the time of the ultrasonic wave transmission and reception, since the influence of the light on the image formation by the ultrasonic wave is not so great, the SOA 415 may be continuously switched on. The timing chart for the case is illustrated in FIG. 8. In this case, the SOA "ON" signal 724 generated by the second delay time 723 is not required, and the second delaying unit 502 and the pulse shaper 505 of the timing control unit 480 can be omitted.

Further, the first delay time and the second delay time are not limited to the description above. For example, the strength of the sweeping light becomes weak near the maximum value and the minimum value of the wavelength sweeping. Then, if the SOA 415 is continuously switched on, the first delay time 721 may be set as illustrated in FIG. 9 so that a period in which the strength of wavelength swept light decreases is more effectively allocated to the ultrasonic wave reception. In this case, if sampling is performed on the optical interference signal at the same timing as in FIG. 8, the third delay time 725 may be set as illustrated in FIG. 9.

Additionally, delay times greater than the time assumed to be required for the ultrasonic wave transmission and reception are set as the second delay time 723 and the third delay time 725 in FIGS. 8 and 9, but the delay times are not limited thereto. The power of the reception signal of the ultrasonic wave is extremely small compared to the power of the transmission signal, and the acousto-optic effect at the time of the ultrasonic wave reception is small. Then, the second delay time may be set so that the optical interference signal sampling is not performed during the ultrasonic wave transmission having great power. That is, the influence of the acousto-optic effect can be decreased by setting the third delay time so as to include the transmission time in which at least the ultrasonic wave oscillation (transmission) is performed.

Additionally, the ultrasonic wave oscillation and the reflected wave reception for one line are performed as one set in FIGS. 8 and 9, but plural sets may be performed for one line. The configuration is illustrated in FIG. 10. In FIG. 10, two sets of the ultrasonic wave oscillation 704 and the ultrasonic wave reception 705 are performed. Additionally, in the example of FIG. 10, since the influence of the reflected wave of the ultrasonic wave is small as described above, the switching-on of the SOA and the sampling of the interference light are started at the timing when the last ultrasonic wave transmission is completed.

In addition, if the timing as described above for at least the ultrasonic wave oscillation and sampling can be secured with respect to the wavelength sweeping, the configuration of the delaying unit in the timing control unit 480 or the like is not limited to the description above. For example, the third delaying unit 503 may be connected so as to delay the signal of the second delaying unit 502.

Additionally, the second delay time 723 or the third delay time 725 may be set in consideration of, for example, the time (reaching time of reflected wave from inside of observation range) required for the ultrasonic wave signal to reciprocate the observation range. Additionally, in this case, according to the observation range assumed for each measuring object, the second delay time 723 or the third delay time 725 may be set by the user using the operation panel 112. The operation panel 112 is an example of a setting means configured to permit the user to set the predetermined period.

Additionally, in the above embodiment, if the light from the wavelength swept light source 408 is started or stopped, the SOA 415 is switched on and off. In other embodiments, the light from the wavelength swept light source 408 may be switched on and off by providing a shutter to the output unit of the wavelength swept light source 408 or providing a light switch such as a Pockels cell to the outlet of the polygon scanning filter 408*b*. The light switch and the shutter represent examples of stopping means. Additionally, the switching may be realized by adjusting a concentration angle and a scan angle of the light to the scanner and causing the duty ratio of the wavelength sweeping to be less than 100% in the wavelength filter using the polygon scanner such as the polygon scanning filter 408*b*. In that case, since the timing for switching on and off the light source is automatically determined, the first delay time 721 is matched so that the ultrasonic wave transmission and reception are performed at the timing at which the light source is switched off.

Additionally, according to the above embodiment, display modes of the constructed ultrasonic tomographic image and the constructed optical tomographic image are not particularly described, but the ultrasonic tomographic image and the optical tomographic image may be configured so that respective tomographic images corresponding to respective positions of the body cavity such as the blood vessel in the axial direction are displayed in parallel, or may be configured so that the respective tomographic images are displayed so as to be superimposed so that the image centers are matched. Additionally, according to the above embodiment, the A/D converter which is the ultrasonic wave data acquisition means and the A/D converter which is the interference light data acquisition means are configured to be different members, but one member can be configured to be used for both functions.

The detailed description above describes a tomographic image generation device and method disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A tomographic image generation device comprising:
a probe unit including a transmitting and receiving unit, an ultrasonic wave transmitting and receiving unit configured to perform ultrasonic wave transmission and reception, and an optical transmitting and receiving unit configured to perform light transmission and reception, the ultrasonic wave transmitting and receiving unit and the optical transmitting and receiving unit being disposed in the transmitting and receiving unit;
a light source configured to generate a wavelength swept light to be transmitted by the optical transmitting and receiving unit;
a photo coupler unit configured to diverge the wavelength swept light output from the light source; and
a computer processor configured to:
acquire ultrasonic wave data to generate a tomographic image for one line of data in respective rotation positions of the transmitting and receiving unit by performing sampling on an ultrasonic wave echo signal obtained from the ultrasonic wave transmitting and receiving unit while rotating;
acquire interference light data by performing sampling on an interference light signal obtained from the optical transmitting and receiving unit while rotating; and
control operation timing of the acquiring of the ultrasonic wave data and the interference light data so that a sampling period for performing sampling on the interference light signal and a predetermined period for ultrasonic wave oscillation of the ultrasonic wave transmitting and receiving unit for the one line of data do not overlap;
detect light having a predetermined wavelength from the wavelength swept light diverged by the photo coupler, and supply a trigger signal to a timing control unit; and
wherein the timing control unit is configured such that the ultrasonic wave transmitting and receiving unit is subjected to oscillation after a first delay time passes from receiving the trigger signal, and the sampling of the interference light signal is started after the predetermined period passes for the one line of data.

2. The tomographic image generation device according to claim 1, wherein the predetermined period includes a period for ultrasonic wave transmission by the ultrasonic wave transmitting and receiving unit.

3. The tomographic image generation device according to claim 1, wherein the predetermined period includes an assumed period from a time at which the ultrasonic wave transmitting and receiving unit oscillates an ultrasonic wave to a time at which a reflected wave of the ultrasonic wave in an observation range returns.

4. The tomographic image generation device according to claim 1, wherein the computer processor is further configured to:

permit a user to set the predetermined period via an operating panel.

5. The tomographic image generation device according to claim 1, wherein the computer processor is further configured to:
stop an output of wavelength swept light by the light source in a period other than the sampling period.

6. The tomographic image generation device according to claim 5, wherein the computer processor is configured to:
stop an output of wavelength swept light by the light source during at least a period for the ultrasonic wave transmission.

7. The tomographic image generation device according to claim 1, further comprising:
a reflecting unit configured to reflect only light having the predetermined wavelength from one of the wavelength swept light diverged by the photo coupler; and
wherein the computer processor is configured to:
detect the light having the predetermined wavelength reflected by the reflecting unit.

8. The tomographic image generation device according to claim 1, wherein a direction of the ultrasonic wave transmission and reception of the ultrasonic wave transmitting and receiving unit and the light transmission and reception of the optical transmitting and receiving unit is perpendicular to the rotary central axis of the probe unit.

9. A method of controlling a tomographic image generation device that generates a tomographic image by using a transmitting and receiving unit, the transmitting and receiving unit having an ultrasonic wave transmitting and receiving unit that performs ultrasonic wave transmission and reception, and an optical transmitting and receiving unit that performs light transmission and reception, and wherein the ultrasonic wave transmitting and receiving unit and the optical transmitting and receiving unit are disposed in the transmitting and receiving unit, the method comprising:
generating a wavelength swept light from a light source to be transmitted by the optical transmitting and receiving unit;
diverging the wavelength swept light output from the light source with a photo coupler unit;
acquiring ultrasonic wave data for generating a tomographic image for one line of data in respective rotation positions of the transmitting and receiving unit by performing sampling respectively on an ultrasonic wave echo signal obtained from the ultrasonic wave transmitting and receiving unit while rotating;
acquiring interference light data by performing sampling on an interference light signal obtained from the optical transmitting and receiving unit while rotating;
controlling operation timing of the acquisition step so that a sampling period for performing sampling on the interference light signal and a predetermined period for ultrasonic wave oscillation of the ultrasonic wave transmitting and receiving unit for the one line of data do not overlap;
detecting light having a predetermined wavelength from the wavelength swept light diverged by the photo coupler;
supplying a trigger signal to a timing control unit;
subjecting the ultrasonic wave transmitting and receiving unit to oscillation after a first delay time passes from receiving the trigger signal from the timing control unit; and
starting the sampling of the interference light signal after the predetermined period passes for the one line of data.

10. The method according to claim 9, further comprising:
stopping an output of wavelength swept light by the light source in a period other than the sampling period.

11. The method according to claim 10, wherein the output of wavelength swept light by the light source is stopped during at least the period for the ultrasonic wave transmission.

12. The method according to claim 9, further comprising:
reflecting only light having the predetermined wavelength from one of the wavelength swept light diverged by the photo coupler with a reflecting unit; and
detecting the light having the predetermined wavelength reflected by the reflecting unit.

13. The method according to claim 9, wherein a direction of the ultrasonic wave transmission and reception of the ultrasonic wave transmitting and receiving unit and the light transmission and reception of the optical transmitting and receiving unit is perpendicular to the rotary central axis of the probe unit.

14. A tomographic image generation device comprising:
a probe unit including a transmitting and receiving unit, the transmitting and receiving unit including i) an ultrasonic wave transmitting and receiving unit configured to perform ultrasonic wave transmission and reception, and ii) an optical transmitting and receiving unit configured to perform light transmission and reception, the ultrasonic wave transmitting and receiving unit and the optical transmitting and receiving unit being disposed in the transmitting and receiving unit;
a light source configured to generate a wavelength swept light to be transmitted by the optical transmitting and receiving unit;
a photo coupler unit configured to diverge the wavelength swept light output from the light source; and
a computer processor configured to:
acquire ultrasonic wave data to generate a tomographic image for one line of data in respective rotation positions of the transmitting and receiving unit by performing sampling on an ultrasonic wave echo signal obtained from the ultrasonic wave transmitting and receiving unit while rotating;
acquire interference light data by performing sampling on an interference light signal obtained from the optical transmitting and receiving unit while rotating;
control operation timing of the acquiring of the ultrasonic wave data and the interference light data, the timing control unit having a delay circuit, the delay circuit configured to delay a sampling period for performing sampling on the interference light signal and a predetermined period for ultrasonic wave oscillation of the ultrasonic wave transmitting and receiving unit for the one line of data;
detect light having a predetermined wavelength from the wavelength swept light diverged by the photo coupler, and supply a trigger signal to a timing control unit;
the timing control unit being configured such that the ultrasonic wave transmitting and receiving unit is subjected to oscillation after a first delay time passes from receiving the trigger signal, and the sampling of the interference light signal is started after the predetermined period passes for the one line of data; and
wherein the sampling period and the predetermined period do not overlap.

15. The tomographic image generation device according to claim 14, wherein the predetermined period includes a period for ultrasonic wave transmission by the ultrasonic wave transmitting and receiving unit.

16. The tomographic image generation device according to claim 14, further comprising:
an operating panel configured to permit a user to set the predetermined period.

17. The tomographic image generation device according to claim 14, further comprising:
a reflecting unit configured to reflect only light having the predetermined wave length from one of the wavelength swept light diverged by the photo coupler; and
wherein the computer processor is configured to:
detect the light having the predetermined wavelength reflected by the reflecting unit.

18. The tomographic image generation device according to claim 14, wherein a direction of the ultrasonic wave transmission and reception of the ultrasonic wave transmitting and receiving unit and the light transmission and reception of the optical transmitting and receiving unit is perpendicular to the rotary central axis of the probe unit.

* * * * *